United States Patent

Hanson

Patent Number: 5,906,486
Date of Patent: May 25, 1999

[54] SELF-LIGATING ORTHODONTIC BRACKETS

[76] Inventor: G. Herbert Hanson, 57 Augusta St., Hamilton, Ontario, Canada, L8N 1P8

[21] Appl. No.: 09/074,009

[22] Filed: May 7, 1998

[51] Int. Cl.$^6$ ................................................. A61C 3/00
[52] U.S. Cl. .................................. 433/11; 433/10; 433/13
[58] Field of Search .................................. 433/10, 11, 13

[56] References Cited

U.S. PATENT DOCUMENTS

| | | | |
|---|---|---|---|
| 3,772,787 | 11/1973 | Hanson | 433/14 |
| 4,197,642 | 4/1980 | Wallshein | 433/11 |
| 4,248,588 | 2/1981 | Hanson | 433/11 |
| 4,443,189 | 4/1984 | Wildman | 433/10 |
| 4,492,573 | 1/1985 | Hanson | 433/11 |
| 4,698,017 | 10/1987 | Hanson | 433/13 |
| 5,094,614 | 3/1992 | Wildman | 433/10 |
| 5,562,444 | 10/1996 | Heiserr et al. | 433/11 |
| 5,586,882 | 12/1996 | Hanson | 433/11 |
| 5,630,715 | 5/1997 | Voudouris | 433/13 |

Primary Examiner—John J. Wilson
Attorney, Agent, or Firm—Rogers & Scott

[57] ABSTRACT

An orthodontic bracket comprises a spring ligating member comprising a thin flat metal strip that embraces the bracket body and is moved thereon between slot closed and open positions. At least the free end part of the spring member labial arm portion that closes the slot is of smaller width in the mesial distal direction than the arch wire slot gingival surface which is provided with a recess of smaller mesial distal width so that it is closed at its mesial and distal ends. The free end part of the labial arm portion extends into the recess to protect the spring member against excessive movement in the labial direction, while the arch wire slot gingival surfaces at the closed mesial and distal ends of the recess are engagable by an arch wire in the slot for application of maximum torque moment from the arch wire to the bracket. The bracket also comprises a labial lingual extending passage in the spring member labial arm portion permitting insertion of a tool for moving the spring member from the slot closed to the slot open position. The bracket body is provided with a slot registering with the passage that enables the tool to engage the spring member occlusal portion thereby permitting the required movement without overstressing the spring member.

12 Claims, 3 Drawing Sheets

FIG. 8
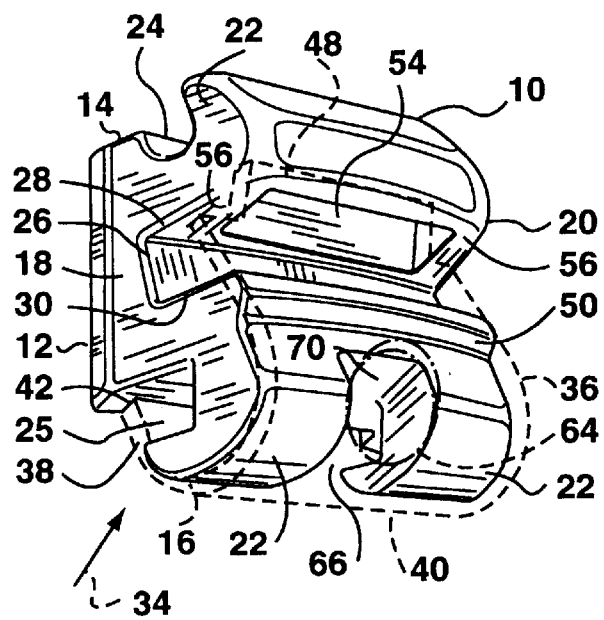
FIG. 9
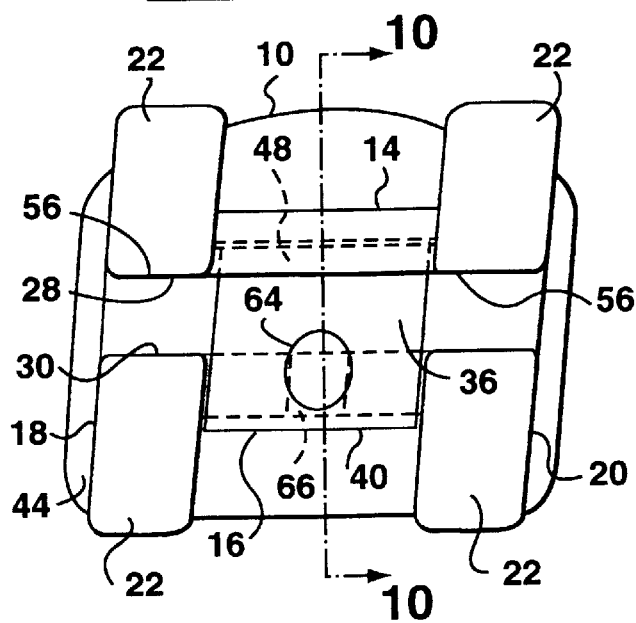
FIG. 10

5,906,486

SELF-LIGATING ORTHODONTIC BRACKETS

FIELD OF THE INVENTION

This invention is concerned with improvements in or relating to self-ligating orthodontic brackets, namely orthodontic brackets which comprise ligating spring means as a permanent part thereof.

REVIEW OF PRIOR ART

The majority of orthodontic procedures employ a plurality of brackets that are attached to respective teeth, usually nowadays by cementing them to the teeth, although they still may be attached to metal bands that embrace the respective teeth. Each bracket has a mesial distal extending slot therein, usually of rectangular cross section in a gingival occlusal plane, and the brackets are connected together using an arch wire, so called because it is preformed to an optimum arch shape corresponding to the desired conformation of the teeth at the conclusion of the procedure. Arch wires of progressively increasing stiffness and, depending on the type of tooth movement to be achieved, also of different cross section, are used one at a time, the wire being retained in the slots by ligating means of some kind. Initially the ligating means usually was a metal wire that was twisted about the bracket and the arch wire; subsequently, upon development of elastomeric materials able to withstand the hostile environment of the human mouth, hoops or loops of such materials are used. In another line of development each bracket comprises a permanently mounted spring ligating member movable on the body between a slot open position for insertion and removal of the arch wire, and a slot closed position for retention of the arch wire in the slot. Specific examples of such brackets are those disclosed and claimed in my U.S. Pat. Nos. 3,772,787; 4,248,588; 4,492,573; and 5,586,882, the disclosures of which are incorporated herein by this reference. These brackets are currently in use in the Hanson SPEED System (Trade Mark) and have proven to be very successful.

There is a constant endeavour in orthodontics to provide brackets that are as efficient, economical and easy to use as possible, especially if orthodontists are to be persuaded to make the changes in their procedures that the adoption of new brackets usually entails. The manufacture of orthodontic brackets is now a mature industry and there is therefore a corresponding requirement to produce them as efficiently and inexpensively as possible in view of the price competition encountered.

Many of the problems involved in the design and use of orthodontic brackets results from their extremely small size, and typically one of my brackets currently in use has a body that measures 2.7 mm to 3.0 mm (0.108 in to 0.120 in) in maximum gingival occlusal dimension, 2.1 mm to 2.7 mm (0.084 in to 0.108 in) in maximum labial lingual dimension, and 2.7 mm to 3.0 mm (0.108 in to 0.120 in) in its widest mesial distal dimension. In all of the Hanson SPEED System brackets the spring ligating member is of U-shape and embraces the bracket body with its two coextending arm portions engaging the labial and lingual surfaces thereof and the base of the U facing the bracket body occlusal surface. The spring ligating member when of stainless steel is usually about 0.125 mm (0.005 in) in thickness and, even when stainless steel of the highest possible elastic modulus is used, the material is stressed surprisingly close to the elastic limit as the member is mounted on the body, and as it is moved between the slot open and closed positions. The amount of displacement required to exceed the elastic limit is very small and, once that limit has been exceeded, for example by the operative carelessly moving the member and/or attempting to force it to close over a stiff arch wire that protrudes too far out of the slot, then it may no longer function as a retaining spring. This may require the bracket to be replaced completely, since it is not usually convenient or even possible for the orthodontist to replace the ligating member "in situ". Such replacement is of course inconvenient and unpleasant both for the orthodontist and the patient.

This problem is considerably mitigated by making the spring ligating member from one of the recently developed so-called shape memory metal alloys, also frequently called superelastic metal alloys, which are highly resistant to overstressing and resultant permanent deformation, as compared to stainless steels. A spring member of such material usually is somewhat thicker than the equivalent stainless steel member, e.g. 0.175 mm (0.007 in), but can be deflected as much as 6–10 times more than the equivalent stainless steel member and still return to the non-deflected state with virtually no permanent set. Such spring ligating members as used in the Hanson SPEED System brackets are disclosed, described in greater detail, and claimed in my U.S. Pat. No. 5,586,882, referred to above. These materials, and their processing, are more expensive than the well established and commonly available stainless steels, so that the resulting brackets are more expensive, and this may deter orthodontists from using them, instead accepting the potential risk that careless handling may render the bracket useless.

The brackets disclosed and claimed in my earlier U.S. Pat. Nos. 3,772,787 and 4,248,588 relied solely upon the spring resistance of the spring member labial arm to labial movement to retain the wire in the slot. Subsequently it was found that the range of action of the retainer member could be extended, while reducing the danger of overstressing the material, by arranging that in the slot closed position the free end of the labial arm extends into a mesial-distal extending retainer slot in the gingival wall of the arch wire slot, whereupon labial movement of this labial arm end is limited by its engagement with the lingual wall of the retainer slot. Such a bracket structure is described and claimed in my U.S. Pat. No. 4,492,573.

Experience has shown that problems can sometimes arise even with such brackets provided with spring member protection. For example, if the arch wire employed is of much smaller gingival occlusal dimension than the arch wire slot the wire can sometimes twist or rotate mesially-distally in the slot to such an extent that it tilts into the retainer slot and becomes engaged therein, so that it can no longer be as effective in moving the tooth to the required orientation. Moreover, the retainer slot usually substantially reduces the labial lingual dimension of the gingival surface of the arch wire slot relative to that of the opposite occlusal surface. In most brackets the labial lingual dimension of the arch wire slot occlusal surface is always somewhat larger than the corresponding dimension of the occlusal surface of an arch wire in the slot, so that the two occlusal surfaces can fully butt against one another. On the other hand the presence of the retainer slot reduces the labial lingual dimension of the slot gingival surface to less than that of the corresponding dimension of the arch wire gingival surface, so that the wire gingival surface protrudes beyond the respective labial slot edge. In such a situation the torque moment that can be applied to the bracket by a twisted arch wire engaging the slot gingival surface is reduced, as compared to the moment that can be applied to a bracket in which the same wire engages the slot occlusal surface, because of the reduction in the length of the effective moment arm. This can cause difficulty in a procedure in which the twisted arch wire is engaged with the gingival slot surface in one bracket and the occlusal slot surface in an adjacent bracket or brackets, in that correspondingly different torque moments are applied to the brackets. The lower torque moment slows the correcting movement of the respective tooth, as compared to the other teeth, while there is a limit to the use of a stiffer wire to increase the torque moment because of the need to ensure that brackets receiving the higher torque moment do not overstress the teeth to which they are attached. This problem is addressed and corrected by the brackets of this invention.

In the Hanson SPEED System brackets the spring member is moved in the gingival direction to close the slot labial mouth and in the occlusal direction to open it, and is positively retained in each of these positions. In practice the member moves very easily to the slot closed position, being virtually self propelled in the closing direction by its resilience as soon as it is disengaged from its retaining surface, so that virtually any conveniently available suitable dental instrument (or even a fingernail) can be used for this purpose. The member is correspondingly much more difficult to move to the slot open position and, in my first U.S. Pat. No. 3,772,787, it was proposed to move it by means of a special pincer-like tool (see FIG. 4 thereof), the tool being used to squeeze the spring member gingivally on the bracket body to the slot-closed position, and having specially shaped ends cooperating with sloping cam faces on the bracket body and engaging between the bracket body and the base of the U to move the member to the slot-open position as the tool ends are moved together. It was found later that such a special tool was not required and currently the spring member is usually moved to slot open position by engaging the gingival end of the spring member lingual arm with a suitable already available dental tool, such as a sickle scaler as used by periodontists, or any other tool with a suitable gooseneck reduced end configuration; the gingival-lingual junction of the bracket body is provided with a recess into which the tool can enter to permit adequate displacement of the spring member lingual arm in the occlusal direction.

Some operatives have found difficulty with this opening procedure in that the free end of the spring member lingual portion protrudes only slightly below the gingival end of the bracket body and cannot readily be seen from the labial. The opening tool usually is therefore engaged purely by feel, such engagement being followed by a relatively hard push of the tool in the occlusal direction in order to get the spring member moving. If the tool is not properly engaged the push may instead wedge the tool between the bracket body recess and the spring member lingual arm, from where it must be disengaged and a new attempt made. It is desirable therefore to provide instead a bracket structure with which secure engagement of the opening tool with the spring member is clearly visible before any attempt is made to move the spring member. The provision of such a structure presents unexpected difficulties which must be overcome.

My U.S. Pat. No. 4,698,017 discloses and claims a different type of self-ligating bracket in which a bracket body 10 (see FIG. 2) has a non-springy ligating member 24 pivotally mounted on the body; the member 24 is held in the slot closed position by a latch spring 42 which engages a sear 38 on the member. The ligating member is unlatched for movement to the slot open position by passing a pointed tool 46 lingually through a passage 50 which opens to the labial surface of the member 24 until the end of the tool engages and flattens the latch spring 42; the tool can then be used to rotate the ligating member to the slot open position. In U.S. Pat. No. 5,562,444, issued Oct. 8, 1996 to Wolfgang HEISER a spring ligation member 12 pivots on the bracket body between a slot open position shown in FIG. 3 and a slot closed position shown in FIG. 2. FIG. 4 shows an embodiment in which a hole 27 is provided in the labial face of member 12 to receive a pointed tool to facilitate such movement.

SUMMARY OF THE INVENTION

It is a principal object of the invention therefore to provide new self-ligating brackets.

It is another principal object to provide new self-ligating brackets provided with protection of the spring ligating member against excessive labial movement, and in which the labial lingual dimension of the arch wire slot gingival surface is at least sufficient for full engagement by the corresponding gingival surface of an arch wire of maximum labial lingual dimension in the slot.

It is a further object to provide new self-ligating brackets with which secure engagement of an opening tool with the spring ligating member is visible labially to an operator.

In accordance with the invention there is provided an orthodontic bracket comprising:

a bracket body having labial, lingual, gingival, occlusal, mesial and distal surfaces, the body having therein a mesial distal extending arch wire slot having lingual, gingival, and occlusal surfaces and opening to the bracket libial surface; and a spring ligating member comprising a thin flat metal strip having coextending labial and lingual arm portions having respective free end parts and connected together by an occlusal connecting portion;

the spring ligating member embracing the bracket body and being movable thereon from a slot closed position in which the slot opening is closed by the labial arm portion for retention thereby of an arch wire in the arch wire slot, to a slot open position in which the slot opening is open for insertion of an arch wire into the arch wire slot;

wherein at least the free end part of the labial arm portion is of smaller width in the mesial distal direction than the arch wire slot gingival surface;

and wherein the bracket body is provided in the arch wire slot gingival surface with a mesially distally extending recess of smaller width in the mesial distal direction than the arch wire slot gingival surface so that it is closed at its mesial and distal ends;

into which recess the free end part of the labial arm portion extends when the spring member is in the slot closed position to retain the labial arm portion against excessive movement in the labial direction under the urge of an arch wire retained thereby in the arch wire slot;

the arch wire slot gingival surfaces at the closed mesial and distal ends of the recess being engagable by an arch wire retained in the slot for application of torque moment from the arch wire to the bracket.

Also in accordance with the invention there is provided an orthodontic bracket comprising:

a bracket body having labial, lingual, gingival, occlusal, mesial and distal surfaces, the body having therein a mesial distal extending arch wire slot having lingual, gingival, and occlusal surfaces and opening to the bracket libial surface portion; and a spring ligating member comprising a thin flat metal strip having coextending labial and lingual arm portions connected together by an occlusal connecting;

the spring ligating member embracing the bracket body and being movable thereon from a slot closed position in which the slot opening is closed by the labial arm portion for retention thereby of an arch wire in the arch wire slot, to a slot open position in which the slot opening is open for insertion of an arch wire into the arch wire slot;

wherein the labial arm portion is provided with a labial lingual extending passage permitting insertion through the labial arm portion of a tool for engagement with the spring member for movement thereof from the slot closed to the slot open position; and wherein the bracket body is provided in registry with the passage with a gingival occlusal extending tool receiving slot extending between its labial and occlusal surfaces and permitting passage therein of the tool and engagement of the tool with at least a part of the spring member occlusal connecting portion prior to the tool imparting movement to the spring member, the tool receiving slot permitting movement of the tool with the spring member in such engagement with the occlusal connecting portion in movement of the spring member from the slot closed to the slot open position.

DESCRIPTION OF THE DRAWINGS

Particular preferred embodiments of the invention will now be described, by way of example, with reference to the accompanying diagrammatic drawings, wherein:

FIG. 8 is a perspective view similar to FIG. 2 of a fourth embodiment in which the mesial distal dimension of the spring member labial portion free end is smaller than that of the remainder of the member;

FIG. 9 is a view from the labial of a fifth embodiment comprising a so-called siamese twin bracket; and FIG. 10 is an occlusal-gingival cross section of the bracket of FIG. 9 taken on the line 10—10 therein.

DESCRIPTION OF THE PREFERRED EMBODIMENTS

Figure 1:
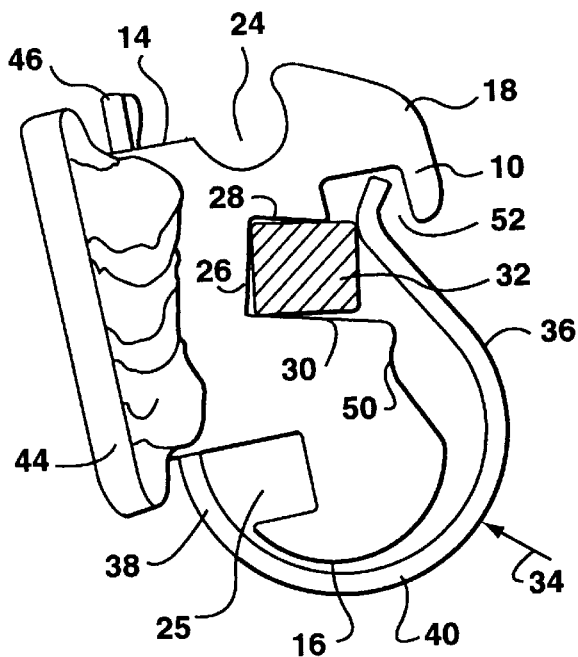
FIG. 1 is a view from the mesial of a prior art bracket, shown with a rectangular cross section arch wire of maximum transverse cross section dimensions in the arch wire slot.
Figure 2:
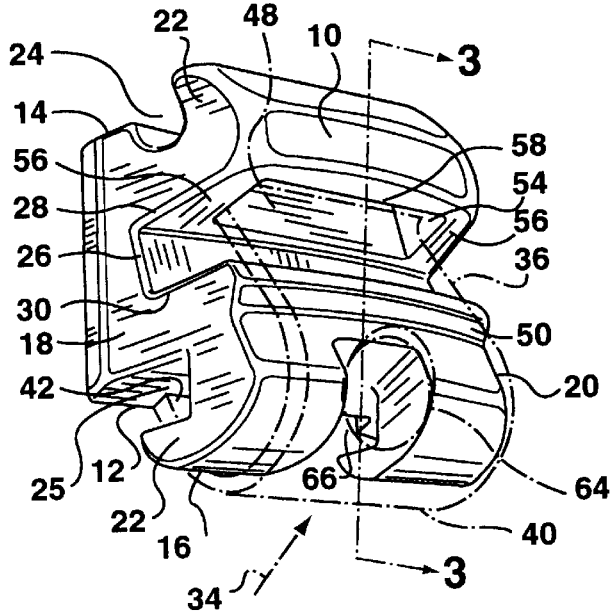
FIG. 2 is a perspective view from the mesial and labial of a first embodiment, showing in broken lines the ligating latch spring member in slot closed position.

In this specification and the appended claims, for convenience in language the brackets and parts thereof are referred to, unless otherwise specified, as they would be used mounted in the upper arch region of a patient's mouth and employed in a labial procedure, even though the brackets may be used for either labial or lingual procedures. As applied to the bracket structure the labial and lingual direction designations are reversed between the two procedures, e.g. the bracket surface referred to as the labial surface in the labial procedure becomes the lingual surface in the lingual procedure, and vice versa, and the arch wire slot opens to the lingual and not the labial. Again for convenience in description the brackets are described as having specific named surfaces but, as will be apparent, smooth exterior contours can only be achieved by avoiding sharp edges and sharp edged junctions wherever possible, and the various surfaces therefore usually merge smoothly with one another without a definite junction between them being apparent.

Similar parts are given the same reference number in all the Figures of the drawings wherever this is appropriate.

The brackets of the invention as described and shown herein are intended for use with the so-called straight wire technique with which each bracket is attached to its respective tooth in an attitude such that, as the arch wire attempts to return to its preformed arch shape and to be straight as seen in a labial-lingual plane, the tooth is moved toward its desired optimized position and attitude. In order for the arch wire to be straight at the conclusion of the procedure the brackets for different teeth must accommodate for the very different inclinations of the tooth surfaces to which they are attached. There are two main methods by which this is done, either by suitable shaping of the bracket bases and of their base surfaces that contact the teeth surfaces, or by changing the inclination of the arch wire slots.

In the brackets shown herein the torque requirements (except rotation about a mesial distal axis), angulation requirements (rotation about a labial lingual axis), and first order pre-adjustments, are obtained by suitable shaping of the bracket bases, particularly of the surface that engages the tooth surface, and by variation of the base thickness, so that when the teeth are in their optimum attitude and rotational position all of the slot surfaces engaged by the arch wire are aligned. Preadjustment of rotation about the mesial-distal axis (crown torque) are made by forming the archwire slots at different angles. The base shapes and slot angles required for the different brackets will be apparent to those skilled in the art and need not be described herein.

Referring now to all of the brackets, the bracket body has labial, lingual, gingival, occlusal, mesial and distal surfaces 10, 12, 14, 16, 18 and 20 respectively. The brackets of FIGS. 1–8 are provided with a single gingivally extending tie wing 22 shaped to provide a respective mesial distal extending groove 24 that opens gingivally for the reception and retention in known manner of external wire tie wires, elastomeric hoop ligatures, and tension and compression members whenever their use is required; the manner in which such orthodontic elements are used is well known to those skilled in the art and does not require explanation or illustration herein. The bracket of FIGS. 9 and 10 is provided with two such tie wings 22, extending gingivally and occlusally and providing respective grooves 24. The body of the brackets of FIGS. 1–8 is also provided with a mesial-distal extending secondary slot 25, which in these embodiments is of rectangular transverse cross section in a gingival occlusal plane, the slot opening approximately at the junction of the lingual and occlusal surfaces 12 and 16, and being available in known manner for the reception of secondary arch wires and other orthodontic elements.

All of the bracket bodies are provided with a mesial-distal extending labially opening arch wire slot, which in these embodiments is of rectangular transverse cross section in a gingival occlusal plane and opens to the labial surface 10, the slot having lingual, gingival and occlusal surfaces 26, 28 and 30 respectively. This slot receives an arch wire 32, which usually in the early stages of a procedure is of circular cross section and of small enough diameter for the bracket to slide freely along it once the arch wire is fully within the slot and fully aligned therein; usually subsequently the round arch wire is replaced by one of rectangular cross section. The arch wire is engaged by a spring ligating member 34, to be described in more detail below, to give a high degree of control for rotation and tipping of the teeth into the desired optimum position.

The spring member 34 retains the arch wire in the slot, and presses it resiliently toward engagement with at least the slot lingual surface 26; in practice the spring member will press the arch wire either toward the junction of the lingual and gingival surfaces, or the junction of the lingual and occlusal surfaces. The member comprises a strip of thin flat springy metal formed generally to a U shape so as to embrace the bracket body and to conform closely to the bracket body gingival occlusal cross section while in the slot closed position, as illustrated in FIGS. 1 to 4, and 6 to 10. For convenience in description the spring member is regarded as comprising opposed coextending labial and lingual portions 36 and 38 respectively, each in embracing sliding engagement with the respective bracket body surface, and a connecting occlusal portion 40. As with the bracket body these different portions 36 through 40 merge smoothly into one another at respective junctions with no specific line of demarcation between them. In these embodiments the spring member is movable by sliding movement gingivally and occlusally on the bracket body between a slot open position shown in FIG. 5 in which the labial mouth of the slot is open for insertion or removal of the arch wire, and the slot closed position in which its labial portion 36 engages the arch wire. The lingual portion 38 is relatively straight along its length and is retained for the sliding movement in a correspondingly extending slot 42 formed in the bracket body lingual surface 12. The slot 42 is closed for retention of the lingual portion therein by a mounting pad 44 (see FIGS. 1, 5 to 7, 9 and 10) attached to the body as, for example, by laser welding, and by which the bracket is attached to the respective tooth. The free end of the lingual portion 38 is dimpled at 46, or otherwise deformed out of its plane, to prevent the spring member from being moved off the bracket body.

The occlusal portion 40 is at least approximately semi-circular, while the labial portion 36 immediately adjacent the occlusal-labial junction is concave toward the bracket body in conforming closely thereto. The remainder of the labial portion is relatively straight and terminates in a free end part 48 that is inclined toward the labial, being shaped so that in slot open position it will engage and be retained by a mesial distal extending parking land 50.

Referring now specifically to FIG. 1, in order to protect the spring member labial portion against excessive labial movement under the action of the arch wire, a prior art bracket such as is shown therein has been provided in the arch wire slot gingival surface with a slot 52 extending from the mesial surface to the distal surface and opening to both of those surfaces, into which slot the end of the spring member labial arm portion 36 can extend when in the slot closed position. The slot must be of substantial labial lingual dimension to permit ready insertion of the spring member end therein while the arch wire is displaced out of the slot, which is the usual starting situation, and to permit the spring member to still engage the arch wire when it is fully inserted in the slot, as at the end of that particular phase of the procedure. As will be seen from FIG. 1, the most usual result is that the presence of the slot reduces the labial lingual dimension of the arch wire slot gingival face 28 to substantially less than the corresponding dimension of the arch wire gingival surface, particularly when the arch wire is of the largest transverse cross section dimensions that can be accommodated in the slot, with the attendant disadvantages discussed above.

In the brackets of the invention the gingival surface 28 is instead provided with a mesially distally extending retaining recess 54 of smaller mesial distal width than the gingival surface, so that it is closed at its mesial and distal ends and thereby provides labial lingual extending gingival rail surfaces 56 (colloquially referred to as torquing rails) at the closed mesial and distal ends, these rail surfaces being engagable by the arch wire gingival surface over the full labial lingual extent thereof for maximum application of torque moment from the arch wire to the bracket. In the embodiments of FIGS. 2–7, 9 and 10 the width dimension of the entire spring member 34 in the mesial distal direction is smaller than that of the slot gingival surface 28, and in particular sufficiently smaller than the mesial distal width of the retaining recess 54 that the free end part 48 of the labial portion can be inserted into the recess when the spring member is in the slot closed position, thereby protecting the portion 36 against excessive labial movement, as required. The labial lingual dimension of the retainer recess 54 is such that the spring member is able to engage the smallest cross-section arch wire with which the bracket is to be used, such as the above-described round arch wire, and is also able to accommodate the largest crosssection wire that is to be used with a small amount of clearance between it and the wire when mesial distal movement along the arch wire is required. The maximum extent of the labial movement that is permitted by the recess 54 is well within the amount that would result in over-stressing and damage to the spring retainer member, even when the member is of stainless steel and not of one of the shape memory metal alloys.

In a standard bracket of the invention the arch wire slot has, for example, a gingival-occlusal dimension of 0.55 mm –0.0 mm and +0.013 mm (0.022 in –0.0 in and +0.0005 in), while the largest rectangular wire used has a nominal gingival-occlusal dimension of 0.53 mm (0.021 in), but is more usually 0.52 mm (0.0205 in); such a largest wire has a nominal lingual-labial dimension of 0.625 mm (0.025 in), and it is this latter dimension that determines the amount of correcting torque that it is able to apply to the bracket. However, it was found that there was little point in using such a wire, or indeed any wire with a nominal lingual-labial dimension of greater than about 0.35 mm (0.014 in) when the torque was to be generated between the wire and slot gingival surfaces, since this was the effective lingual-labial dimension of the slot labial face in the presence of the prior art open-ended retaining slot 52. In a bracket of the invention such a wire is able to maintain engagement of its gingival surface over the full extent of its labial-lingual dimension with the slot gingival surface via the torquing rails 56, so that it will be effective to the maximum possible extent and to the same extent as the torque force produced between fully spring member engaged occlusal faces of the arch wire and the bracket slot.

For ease of manufacture the recess 54 may be provided by forming a passage that extends completely through the bracket body from the slot gingival surface 28 to the gingival ligature receiving groove 24, as is most clearly seen in FIGS.

3 and 5–7. It is important that the mesial distal recess surface 58 closer to the bracket body labial surface does not slope labially toward the occlusal, since in the slot closed position and with the free end part 48 engaging such a slanting surface, it would act as an opening cam tending to move the spring member toward the slot open position. The surface 58 is therefore formed to be more or less parallel to the gingival occlusal plane. Again, from the point of view of ease of manufacture, this parallel surface 58 conveniently is provided by cutting, or otherwise forming, a narrow mesial distal extending slot 60 as shown in FIGS. 4–7 at the labial side of the recess 54. The slot 60 is sufficiently spaced from the slot lingual wall 26, and is sufficiently narrow in the labial lingual dimension, that the resulting remaining torquing surfaces 56 are long enough, e.g. 0.71 mm (0.028 in), for the gingival surface of a rectangular arch wire of maximum labial lingual dimension to be fully engaged with them.

Figure 5:
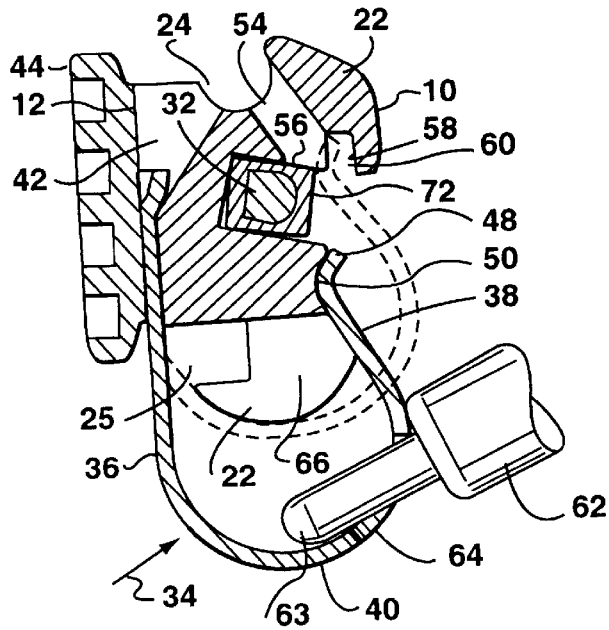
FIGS. 5 and 6 are similar cross sections in a gingival occlusal plane through the bracket of FIG. 4 showing the spring ligating member respectively in slot open and slot closed positions, and illustrating the manner in which an opening tool is used to effect the opening movement.
Figure 6:
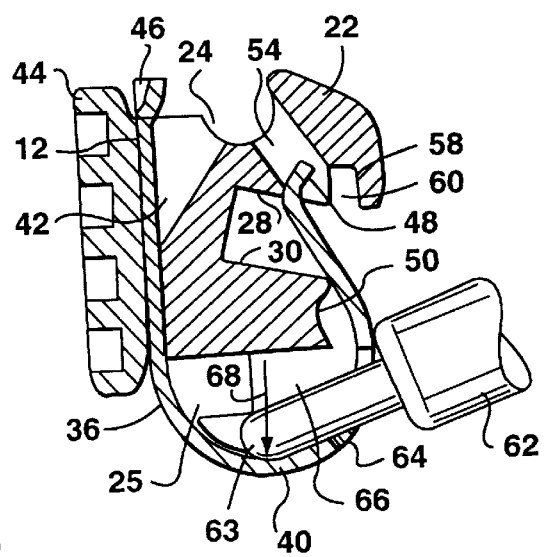

FIG. 5 shows the manner in which the torquing rails provided by the invention facilitate the use of a small transverse cross section arch wire in combination with individual cooperating sleeves, as first described and claimed in my U.S. Pat. No. 5,380,197, the disclosure of which is incorporated herein by this reference. As shown the small cross section wire 32, in this embodiment of D-shape cross section and of transverse dimension 0.45 mm (0.018 in), is embraced by a rectangular cross section friction-fit torquing sleeve 72 of maximum transverse dimensions, while in the absence of such a sleeve the wire is free to slide posteriorly.

In the embodiment shown in FIG. 8 the mesial distal dimension of the spring member 34 is almost equal to that of the bracket body, so that the maximum spring effect can be obtained from the member, and only the lingual portion end part 48 has the smaller mesial distal dimension required for it to be able to enter the retainer recess 54.

The movement of the spring member to the slot open position may be carried out with the brackets of the invention by use of an elongated pointed tool 62 that is passed through a labial lingual extending passage 64, which is provided in the labial portion of the spring member so that it is readily accessible by the tool. This passage registers with a gingival occlusal slot 66, extending between the bracket body labial and occlusal surfaces 10 and 14, through which the tool can pass and engage with at least a part of the spring member occlusal connecting portion 40 prior to the tool being moved to impart movement to the spring member, such movement being indicated by the arrow 68 in FIGS. 3, 6, 7 and 10. The slot permits the tool to remain in such engagement with the occlusal connecting portion during the movement of the spring member from the slot closed to the slot open position.

It is important from the point of view of visibility to an operator that the tool engaging opening be provided in the labial portion of the spring member, but it also important that the tool is able to engage at least a part of the spring member occlusal portion during at least the initial part of the opening movement. In the absence of any such occlusal engagement the movement of the tool in the occlusal direction primarily tends to move only the labial portion 36 with corresponding deformation of the occlusal portion 40, while the lingual portion 38 tends to tilt and become frictionally engaged with the walls of its guide slot 42. The effect of the distortion and frictional engagement is to require even more opening force to be applied, and it easily becomes excessive, to the point that the spring member is overstressed and its effectiveness destroyed. With the brackets of the invention, as long as the operator ensures that the tool is fully inserted through the passage 64 and into the slot 66, the positive engagement of the tool with the occlusal portion during the opening movement ensures that such overstressing will not occur. The positive opening action is facilitated by providing a mesial distal bracket body surface 70 that slopes lingually and occlusally to form a wedge-shaped space between itself and the adjacent concave occlusal surface of the spring member. This surface is engaged by the tool and acts as a ramp moving the tool occlusally in the direction of the arrow 68 and into the required engagement. A suitable dimension for the passage 64 is, for example, a diameter of from 0.375 mm (0.015 in) to 0.50 mm (0.020 in).

Figure 3:
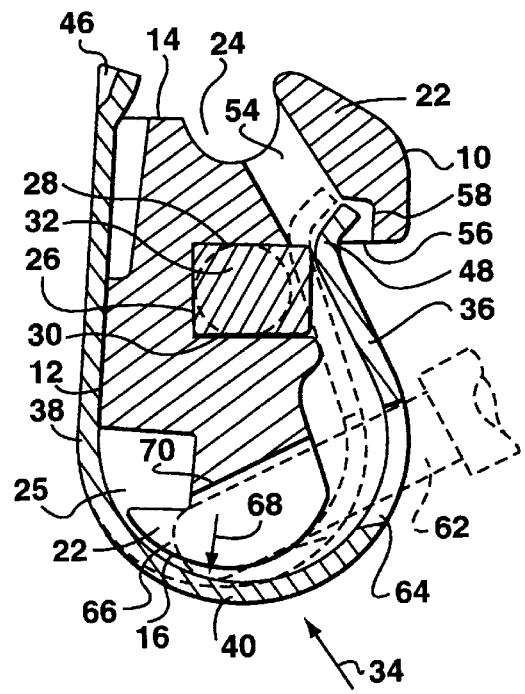
FIG. 3 is a cross section in a gingival occlusal plane through the bracket of FIG. 2, taken on the line 3—3 therein, showing in solid lines an arch wire of rectangular transverse cross section in the arch wire slot and the corresponding position of the spring member labial portion; showing in broken lines an arch wire of circular transverse cross section in the arch wire slot and the corresponding position of the spring member labial portion; and illustrating the manner in which an opening tool is used in conjunction therewith.
Figure 4:
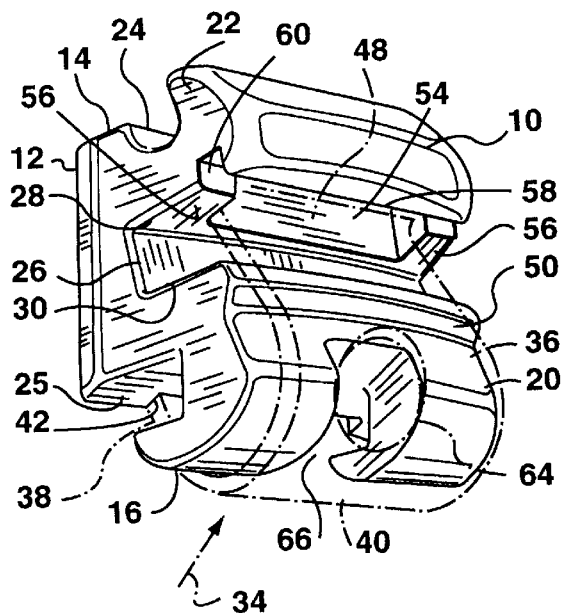
FIG. 4 is a perspective view similar to FIG. 2 of a second embodiment illustrating a particular method of making a retainer recess of the invention.
Figure 7:
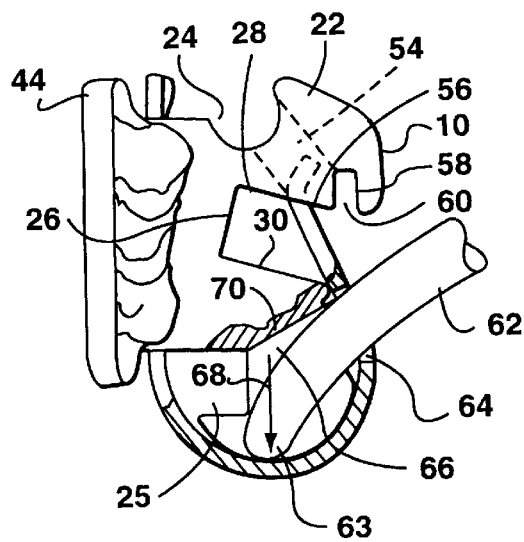
FIG. 7 is a cross section similar to FIGS. 5 and 6 through a bracket which is a third embodiment and showing another form of opening tool for use therewith.

FIGS. 3 and 5 show one form that can be taken by the tool consisting of a body of sufficiently large diameter to be held easily by the operator and a straight extending tip 63 of the reduced diameter required for insertion in the passage 64, e.g. 0.375 mm (0.015 in). With such a tool preferably the passage 64 is formed as close as possible to the occlusal portion to ensure the required occlusal portion engagement. FIG. 7 shows another form that can be taken by the tool in which the tip 63 is curved and is held with the tip curving toward the occlusal; this permits the passage 64 to be located somewhat further from the occlusal than with the embodiments of FIGS. 3 and 5. Such a tool can be formed readily by rounding and thereby blunting the tip of a standard dental explorer.

FIGS. 9 and 10 show the application of the invention to a bracket of the so-called siamese twin type comprising two mesially distally spaced pairs of tie wings 22 with the spring member 34 mounted on the bracket body between them. The passage 64 is in this embodiment disposed with its occlusal edge at the junction of the spring member labial portion 36 with the occlusal portion 40, so that it is as close as possible to the occlusal portion. The tip of the tool 62 immediately engages the ramp surface 70 and the occlusal portion 40 as it is inserted through the passage 64.

I claim:

1. An orthodontic bracket comprising:

a bracket body having labial, lingual, gingival, occlusal, mesial and distal surfaces, the body having therein a mesial distal extending arch wire slot having lingual, gingival, and occlusal surfaces and opening to the bracket labial surface; and a spring ligating member comprising a thin flat metal strip having coextending labial and lingual arm portions having respective free end parts and connected together by an occlusal connecting portion;

the spring ligating member embracing the bracket body and being movable thereon from a slot closed position in which the slot opening is closed by the labial arm portion for retention thereby of an arch wire in the arch wire slot, to a slot open position in which the slot opening is open for insertion of an arch wire into the arch wire slot;

wherein at least the free end part of the labial arm portion is of smaller width in the mesial distal direction than the arch wire slot gingival surface;

and wherein the bracket body is provided in the arch wire slot gingival surface with a mesially distally extending recess of smaller width in the mesial distal direction than the arch wire slot gingival surface so that it is closed at its mesial and distal ends;

into which recess the free end part of the labial arm portion extends when the spring member is in the slot closed position to retain the labial arm portion against excessive movement in the labial direction under the urge of an arch wire retained thereby in the arch wire slot;

the arch wire slot gingival surfaces at the closed mesial and distal ends of the recess being engagable by an arch wire retained in the slot for application of torque moment from the arch wire to the bracket.

2. A bracket as claimed in claim 1, wherein the bracket body recess is provided by a passage extending through the bracket body from the arch wire slot gingival surface to the bracket body occlusal surface.

3. A bracket as claimed in claim 2, wherein the bracket body recess labial surface is provided by a mesial distal extending narrow slot extending between the bracket body mesial and distal surfaces.

4. A bracket as claimed in claim 1, wherein the bracket body recess labial surface is provided by a mesial distal extending narrow slot extending between the bracket body mesial and distal surfaces.

5. A bracket as claimed in claim 1, wherein the spring member labial portion that extends into the bracket body recess is of smaller width in the mesial distal direction than the remainder of the spring member.

6. An orthodontic bracket comprising:

a bracket body having labial, lingual, gingival, occlusal, mesial and distal surfaces, the body having therein a mesial distal extending arch wire slot having lingual, gingival, and occlusal surfaces and opening to the bracket labial surface; and a spring ligating member comprising a thin flat metal strip having coextending labial and lingual arm portions having respective free end parts and connected together by an occlusal connecting portion;

the spring ligating member embracing the bracket body and being movable thereon from a slot closed position in which the slot opening is closed by the labial arm portion for retention thereby of an arch wire in the arch wire slot, to a slot open position in which the slot opening is open for insertion of an arch wire into the arch wire slot;

wherein at least the free end part of the labial arm portion is of smaller width in the mesial distal direction than the arch wire slot gingival surface;

wherein the bracket body is provided in the arch wire slot gingival surface with a mesially distally extending recess of smaller width in the mesial distal direction than the arch wire slot gingival surface so that it is closed at its mesial and distal ends;

into which recess the free end part of the labial arm portion extends when the spring member is in the slot closed position to retain the labial arm portion against excessive movement in the labial direction under the urge of an arch wire retained thereby in the arch wire slot;

the arch wire slot gingival surfaces at the closed mesial and distal ends of the recess being engagable by an arch wire retained in the slot for application of torque moment from the arch wire to the bracket;

wherein the spring member labial arm portion is provided with a labial lingual extending passage permitting insertion therethrough of a tool for engagement with the spring member for movement thereof from the slot closed to the slot open position; and wherein the bracket body is provided in registry with the passage with a gingival occlusal extending tool receiving slot extending between its labial and occlusal surfaces and permitting passage therein of the tool and engagement of the tool with at least a part of the spring member occlusal connecting portion prior to the tool imparting movement to the spring member, the tool receiving slot permitting movement of the tool with the spring member in such engagement with the occlusal connecting portion in movement of the spring member from the slot closed to the slot open position.

7. A bracket as claimed in claim 6, wherein the passage is provided as close as possible to the junction of the spring member labial and occlusal portions and the registering slot is provided as close as possible to the junction of the bracket body labial and occlusal surfaces.

8. A bracket as claimed in claim 6, wherein the tool receiving slot comprises a mesial distal surface sloping lingually and occlusally and engagable by the tool as it is inserted through the passage to move the tool occlusally into engagement with the spring member occlusal portion.

9. An orthodontic bracket comprising:

a bracket body having labial, lingual, gingival, occlusal, mesial and distal surfaces, the body having therein a mesial distal extending arch wire slot having lingual, gingival, and occlusal surfaces and opening to the bracket labial surface portion; and a spring ligating member comprising a thin flat metal strip having coextending labial and lingual arm portions connected together by an occlusal connecting portion;

the spring ligating member embracing the bracket body and being movable thereon from a slot closed position in which the slot opening is closed by the labial arm portion for retention thereby of an arch wire in the arch wire slot, to a slot open position in which the slot opening is open for insertion of an arch wire into the arch wire slot;

wherein the labial arm portion is provided with a labial lingual extending passage permitting insertion through the labial arm portion of a tool for engagement with the spring member for movement thereof from the slot closed to the slot open position; and wherein the bracket body is provided in registry with the passage with a gingival occlusal extending tool receiving slot extending between its labial and occlusal surfaces and permitting passage therein of the tool and engagement of the tool with at least a part of the spring member occlusal connecting portion prior to the tool imparting movement to the spring member, the tool receiving slot permitting movement of the tool with the spring member in such engagement with the occlusal connecting portion in movement of the spring member from the slot closed to the slot open position.

10. A bracket as claimed in claim 9, wherein the passage is provided as close as possible to the junction of the spring member labial and occlusal portions and the registering slot is provided as close as possible to the junction of the bracket body labial and occlusal surfaces.

11. A bracket as claimed in claim 10, wherein the tool receiving slot comprises a mesial distal surface sloping lingually and occlusally and engagable by the tool as it is inserted through the passage to move the tool occlusally into engagement with the spring member occlusal portion.

12. A bracket as claimed in claim 9, wherein the tool receiving slot comprises a mesial distal surface sloping lingually and occlusally and engagable by the tool as it is inserted through the passage to move the tool occlusally into engagement with the spring member occlusal portion.

* * * * *